(12) United States Patent
Yoneyama et al.

(10) Patent No.: US 12,312,605 B2
(45) Date of Patent: May 27, 2025

(54) RIBOFLAVIN DERIVATIVE-CONTAINING MEDIUM

(71) Applicant: AJINOMOTO CO., INC., Tokyo (JP)

(72) Inventors: Kazuya Yoneyama, Kawasaki (JP); Kotoe Koseki, Kawasaki (JP); Mizuho Yokoyama, Kawasaki (JP); Satoru Okamoto, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 680 days.

(21) Appl. No.: 16/727,449

(22) Filed: Dec. 26, 2019

(65) Prior Publication Data

US 2020/0208120 A1    Jul. 2, 2020

Related U.S. Application Data

(63) Continuation of application No. PCT/JP2018/024405, filed on Jun. 27, 2018.

(30) Foreign Application Priority Data

Jun. 27, 2017  (JP) ................................. 2017-125164

(51) Int. Cl.
*C12N 5/073*   (2010.01)
*C12N 5/0735*  (2010.01)
*C12N 5/074*   (2010.01)

(52) U.S. Cl.
CPC ......... *C12N 5/0696* (2013.01); *C12N 5/0606* (2013.01); *C12N 2500/32* (2013.01); *C12N 2500/38* (2013.01); *C12N 2500/40* (2013.01); *C12N 2500/60* (2013.01)

(58) Field of Classification Search
CPC ................ C12N 5/0696; C12N 5/0606; C12N 2500/32; C12N 2500/38; C12N 2500/40; C12N 2500/60; C12N 2533/90; C12N 5/10
See application file for complete search history.

(56) References Cited

U.S. PATENT DOCUMENTS

| 5,126,261 | A | * | 6/1992 | Morris ................ C12N 5/0037 435/378 |
| 6,048,728 | A | | 4/2000 | Inlow et al. |
| 2003/0017588 | A1 | | 1/2003 | De Bruijn et al. |
| 2005/0101011 | A1 | | 5/2005 | Tsao |
| 2006/0084168 | A1 | | 4/2006 | Thomson et al. |
| 2010/0261276 | A1 | | 10/2010 | Park et al. |
| 2017/0191025 | A1 | * | 7/2017 | Shimoni ............... C12N 5/0037 |
| 2018/0066268 | A1 | * | 3/2018 | Mermod ................ C12N 15/63 |

FOREIGN PATENT DOCUMENTS

| CN | 101658533 A | 3/2010 |
| CN | 103261404 A | 8/2013 |
| CN | 104781394 A | 7/2015 |
| CN | 104812891 A | 7/2015 |
| CN | 105283541 A | 1/2016 |
| CN | 105637086 A | 6/2016 |
| CN | 106701672 A | 5/2017 |
| JP | 4-501660 A | 3/1992 |
| JP | 9-107955 A | 4/1997 |
| JP | 2003-518378 A | 6/2003 |
| JP | 2007-505625 A | 3/2007 |
| JP | 2008-512122 A | 4/2008 |
| JP | 2010-534072 A | 11/2010 |
| WO | WO 90/03430 A1 | 4/1990 |
| WO | WO1990003430 A1 * | 4/1990 |
| WO | WO 01/48147 A1 | 7/2001 |
| WO | WO 2005/028626 A2 | 3/2005 |
| WO | WO 2006/029197 A1 | 3/2006 |
| WO | WO 2009/014272 A1 | 1/2009 |
| WO | WO 2010/036767 A1 | 4/2010 |
| WO | WO 2011/079004 A1 | 6/2011 |
| WO | WO-2011067465 A1 * | 6/2011 | ........... C12N 5/0606 |
| WO | WO-2015022541 A1 * | 2/2015 | ........... C12N 5/0604 |

OTHER PUBLICATIONS

Dong et al. "Culture of human epidermal stem cells in different media and their biological characteristics." Chinese journal of reparative and reconstructive surgery , 2005, vol. 19(4), Abstract. (Year: 2005).*
Maguire et al. "Medium-mediated effects increase cell killing in a human keratinocyte cell line exposed to solar-simulated radiation." Int J Radiat Biol. Jan. 2011;87(1):98-111. (Year: 2011).*
Baier et al. "Singlet Oxygen Generation by UVA Light Exposure of Endogenous Photosensitizers" Biophys J. Aug. 15, 2006;91(4):1452-9. (Year: 2006).*
International Search Report issued on Oct. 2, 2018 in PCT/JP2018/024405 (with English translation), 5 pages.
Masato Nakagawa, et al., "A Novel Efficient Feeder-Free Culture System for the Derivation of Human Induced Pluripotent Stem Cells" Scientific Reports, vol. 4, Jan. 2014, 8 pages.
Tenneille E. Ludwig, et al., "Derivation of Human Embryonic Stem Cells in Defined Conditions" Nature Biotechnology. Brief Communications, vol. 24, No. 2, Feb. 2006, pp. 185-187 and cover page.
Guokai Chen, et al., "Chemically Defined Conditions for Human iPSC Derivation and Culture" Nature Methods, vol. 8, No. 5, May 2011. 8 pages.
Extended European Search Report issued Apr. 14, 2021 in European Patent Application No. 18823134.4, 10 pages.
Muhammad Ali Sheraz, et al., "Photo, Thermal and Chemical Degradation of Riboflavin" Beilstein Journal of Organic Chemistry, vol. 10, XP055318326, Aug. 26, 2014, pp. 1999-2012.

(Continued)

*Primary Examiner* — Titilayo Moloye

(74) *Attorney, Agent, or Firm* — Oblon, McClelland, Maier & Neustadt, L.L.P.

(57) ABSTRACT

A medium which contains a riboflavin derivative is useful for proliferating and culturing pluripotent stem cells such as iPS cells and ES cells, and is free from degradation due to storage as complete medium.

21 Claims, 5 Drawing Sheets

(56) References Cited

OTHER PUBLICATIONS

Alisa Schnellbaecher, et al., "Vitamins in Cell Culture Media: Stability and Stabilization Strategies" Biotechnology and Bioengineering, vol. 116, No. 6, XP055736111, Jun. 11, 2019, pp. 1537-1555.

Dong et al., Chinese Journal of Reparative and Reconstructive Surgery, 2005, vol. 19(4), p. 314-317, 2005 (with English machine translation).

Culture Reagents for Mouse Keratinocyte Stem Cells, HAP Culture Collections (https://www.culturecollections.org.uk/media/58032/Culture_Reagents_for_Mouse_Keratinocyte_Stem_Cells.pdf).

* cited by examiner

Matrigel culture results iMatrix-511 culture results

RIBOFLAVIN DERIVATIVE-CONTAINING MEDIUM

CROSS REFERENCES TO RELATED APPLICATIONS

This application is a continuation of International Patent Application No. PCT/JP2018/024405, filed on Jun. 27, 2018, and claims priority to Japanese Patent Application No. 2017-125164, filed on Jun. 27, 2017, both of which are incorporated herein by reference in their entireties.

BACKGROUND OF THE INVENTION

Field of the Invention

The present invention relates to media for proliferating a stem cell, particularly a pluripotent stem cell, which media are superior in storage stability, particularly, stability when stored in a liquid as a complete medium. The present invention also relates to methods for producing such a medium and method for proliferating a stem cell in such a medium.

Discussion of the Background

In regenerative medicine, using stem cells such as iPS cell and ES cell, it is assumed that these cells are to be efficiently proliferated, thereafter differentiated into target tissues and transplanted. Various media aiming at proliferation of cells have been reported (see—Nakagawa M., et al., Sci Rep. 2014; 4:3594; Ludwig T. E., et al., Nat. Biotechnol., 2006; 24:185; and Chen, G., et al., Nat Methods, 2011; 8:424, all of which are incorporated herein by reference in their entireties) and are commercially available. Many of them are composed of a plurality of bottles containing various components and they are used after mixing. The mixture is generally referred to as a "complete medium".

The plurality of bottles contain, for example, a basal medium composed of amino acids, vitamins, minerals, buffering agents and the like, and supplements composed of proteins and the like. The supplements are further classified into two or more depending on the type and stored. These are provided as refrigerated products or frozen products.

In general, a medium for stem cell proliferation is produced by mixing a basal medium and a supplement (one or a plurality of supplements) at the time of use to give a complete medium and stored as a liquid. The complete medium can be generally stored for about two weeks. In fact, however, there were some cases where cells did not grow when a complete medium stored for 2 weeks was used and the cause thereof was unknown.

In regenerative medicine, a system capable of stably culturing and supplying cells is indispensable, and development of a medium therefor and a method for producing the medium is demanded.

SUMMARY OF THE INVENTION

Accordingly, it is one object of the present invention to provide a medium for proliferating and culturing cells, particularly pluripotent stem cells such as iPS cell and ES cell.

It is another object of the present invention to provide a cell proliferation medium that is highly stable in a liquid state, a method for producing the medium, and the like.

These and other objects, which will become apparent during the following detailed description, have been achieved by the inventors' discoveries that riboflavin (RFV) is essential for cell growth, but causes degradation of a medium during storage in a liquid state and that a medium can be stored without degradation by using riboflavin derivatives (RFV derivatives) such as flavin adenine dinucleotide (FAD), flavin mononucleotide (FMN), riboflavin tetrabutyrate (RTB) and the like rather than RFV, which resulted in the completion of the present invention.

That is, the present invention provides the following.

(1) A medium for stem cell proliferation, comprising a riboflavin derivative.

(2) The medium of the above-mentioned (1), wherein the riboflavin derivative is at least one kind selected from the group consisting of flavin adenine dinucleotide, flavin mononucleotide, riboflavin tetrabutyrate, salts thereof and hydrates thereof.

(3) The medium of the above-mentioned (1) or (2), wherein the riboflavin derivative is flavin adenine dinucleotide or a salt thereof, or a hydrate thereof (preferably, flavin adenine dinucleotide disodium salt hydrate).

(4) The medium of any of the above-mentioned (1) to (3), wherein the stem cell is an ES cell or an iPS cell.

(5) The medium of any of the above-mentioned (1) to (4), wherein the medium does not comprise riboflavin.

(6) A medium for stem cell proliferation, comprising a mixture of a basal medium comprising an amino acid, a vitamin, a mineral and a buffering agent and one or more supplements, wherein the basal medium comprises a riboflavin derivative.

(7) The medium of the above-mentioned (6), wherein the riboflavin derivative is at least one kind selected from the group consisting of flavin adenine dinucleotide, flavin mononucleotide, riboflavin tetrabutyrate, salts thereof and hydrates thereof.

(8) The medium of the above-mentioned (6) or (7), wherein the riboflavin derivative is flavin adenine dinucleotide or a salt thereof, or a hydrate thereof (preferably, flavin adenine dinucleotide disodium salt hydrate).

(9) The medium of any of the above-mentioned (6) to (8), wherein the stem cell is an ES cell or an iPS cell.

(10) The medium of any of the above-mentioned (6) to (9), wherein the medium does not comprise riboflavin.

(11) A stabilizer of a medium for stem cell proliferation comprising a riboflavin derivative.

(12) The stabilizer of the above-mentioned (11), wherein the riboflavin derivative is at least one kind selected from the group consisting of flavin adenine dinucleotide, flavin mononucleotide, riboflavin tetrabutyrate, salts thereof and hydrates thereof.

(13) The stabilizer of the above-mentioned (11) or (12), wherein the riboflavin derivative is flavin adenine dinucleotide or a salt thereof, or a hydrate thereof (preferably, flavin adenine dinucleotide disodium salt hydrate).

(14) The stabilizer of any of the above-mentioned (11) to (13), wherein the stem cell is an ES cell or an iPS cell.

(15) A method for stabilizing a medium for stem cell proliferation, comprising adding a riboflavin derivative.

(16) The method of the above-mentioned (15), wherein the riboflavin derivative is at least one kind selected from the group consisting of flavin adenine dinucleotide, flavin mononucleotide, riboflavin tetrabutyrate, salts thereof and hydrates thereof.

(17) The method of the above-mentioned (15) or (16), wherein the riboflavin derivative is flavin adenine dinucleotide or a salt thereof, or a hydrate thereof (preferably, flavin adenine dinucleotide disodium salt hydrate).

(18) The method of any of the above-mentioned (15) to (17) wherein the stem cell is an ES cell or an iPS cell.

(19) A method for producing a medium for stem cell proliferation, comprising adding a riboflavin derivative.

(20) The method of the above-mentioned (19), wherein the riboflavin derivative is at least one kind selected from the group consisting of flavin adenine dinucleotide, flavin mononucleotide, riboflavin tetrabutyrate, salts thereof and hydrates thereof.

(21) The method of the above-mentioned (19) or (20), wherein the riboflavin derivative is flavin adenine dinucleotide or a salt thereof, or a hydrate thereof (preferably, flavin adenine dinucleotide disodium salt hydrate).

(22) The method of any of the above-mentioned (19) to (21), wherein the stem cell is an ES cell or an iPS cell.

(23) A method for producing a medium for stem cell proliferation, comprising mixing a riboflavin derivative, a basal medium comprising an amino acid, a vitamin, a mineral and a buffering agent, and one or more supplements.

(24) The method of the above-mentioned (23), wherein the riboflavin derivative is at least one kind selected from the group consisting of flavin adenine dinucleotide, flavin mononucleotide, riboflavin tetrabutyrate, salts thereof and hydrates thereof.

(25) The method of the above-mentioned (23) or (24), wherein the riboflavin derivative is flavin adenine dinucleotide or a salt thereof, or a hydrate thereof (preferably, flavin adenine dinucleotide disodium salt hydrate).

(26) The method of any of the above-mentioned (23) to (25), wherein the stem cell is an ES cell or an iPS cell.

(27) A method for culturing a stem cell, comprising culturing in the medium of any of the above-mentioned (1) to (10).

(28) A method for producing a stem cell, comprising culturing in the medium of any of the above-mentioned (1) to (10).

(29) A medium for stem cell proliferation, comprising a riboflavin derivative, an amino acid, a vitamin, a mineral, a buffering agent and one or more supplements.

(30) The medium of the above-mentioned (29), wherein the riboflavin derivative is at least one kind selected from the group consisting of flavin adenine dinucleotide, flavin mononucleotide, riboflavin tetrabutyrate, salts thereof and hydrates thereof.

(31) The medium of the above-mentioned (29) or (30), wherein the riboflavin derivative is flavin adenine dinucleotide or a salt thereof, or a hydrate thereof (preferably, flavin adenine dinucleotide disodium salt hydrate).

(32) The medium of any of the above-mentioned (29) to (31), wherein the stem cell is an ES cell or an iPS cell.

(33) The medium of any of the above-mentioned (29) to (32), wherein the medium does not comprise riboflavin.

Effect of the Invention

According to the present invention, a medium for cell proliferation can be provided that can avoid a lowering of performance in cell proliferation even when a complete medium in liquid is stored. As a result, more cells, in particular, pluripotent stem cells such as ES cell, iPS cell and the like can be efficiently obtained, and a large amount of cells can be supplied for use in research, medicine, and the like.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
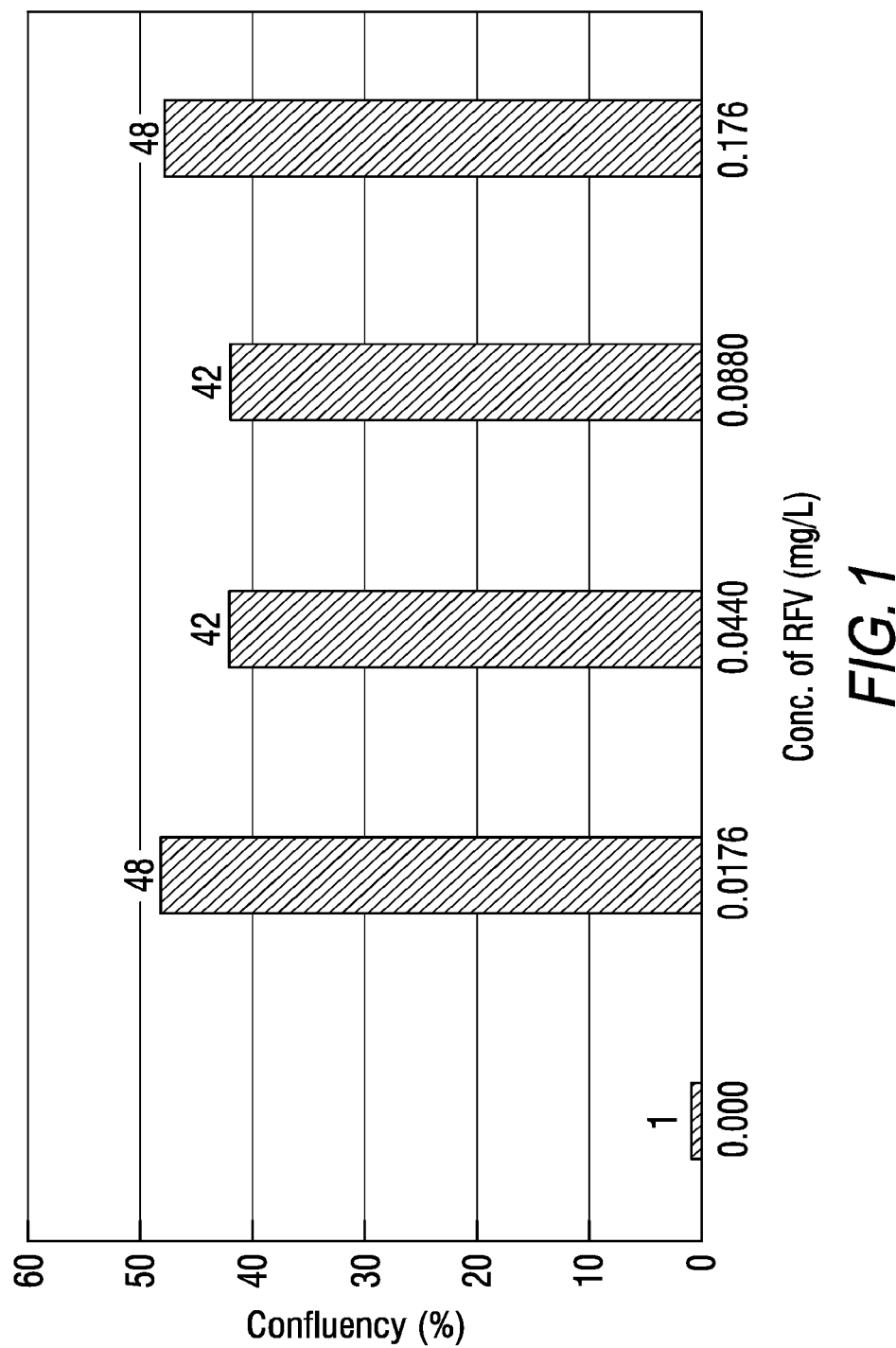
FIG. 1 is a graph showing the study results of the effectiveness of RFV during iPS cell culture (when $Fe^{2+}$ content and $Zn^{2+}$ content were both 25 mol % of the basal medium). The vertical axis shows the cell confluency (%) and the horizontal axis shows the RFV concentration.

The present invention is described below. The terms used in the present specification have meanings generally used in the art unless particularly specified.

In the present invention, the "stem cell" means an immature cell having self-renewal capacity and differentiation/proliferation capacity. The stem cell includes subpopulation such as pluripotent stem cell, multipotent stem cell, unipotent stem cell and the like, according to the differentiation potency. The pluripotent stem cell means a cell capable of differentiating into any tissue or cell constituting living organisms. The multipotent stem cell means a cell capable of differentiating into plural, though not all, kinds of tissues and cells. The unipotent stem cell means a cell capable of differentiating into specific tissues and cells.

Examples of the pluripotent stem cell include embryonic stem cells (ES cell), embryonic germ cell (EG cell), induced pluripotent stem cell (iPS cell), pluripotent stem cell induced and selected by stress or cell stimulation and the like. A stem cell established by cultivating an early embryo generated by nuclear transplantation of the nucleus of a somatic cell is also preferable as the pluripotent stem cell (see Nature, 385, 810 (1997); Science, 280, 1256 (1998); Nature Biotechnology, 17, 456 (1999); Nature, 394, 369 (1998); Nature Genetics, 22, 127 (1999); Proc. Natl. Acad. Sci. USA, 96, 14984 (1999); and Nature Genetics, 24, 109 (2000), all of which are incorporated herein by reference in their entireties).

Examples of the multipotent stem cell include somatic stem cells such as mesenchymal stem cell, hematopoietic stem cell, neural stem cell, myeloid stem cell and germ line stem cell, and the like. The multipotent stem cell is preferably a mesenchymal stem cell, more preferably a bone marrow mesenchymal stem cell. The mesenchymal stem cell broadly means a population of stem cells or progenitor cells thereof, which can differentiate into all or some of the mesenchymal cells, such as osteoblast, chondroblast, lipoblast and the like.

The stem cell targeted in the present invention is preferably a pluripotent stem cell, more preferably an ES cell and an iPS cell, particularly preferably an iPS cell.

The stem cell targeted in the present invention can be preferably used for proliferation of stem cells derived from any animals. The stem cells cultured by using the medium of the present invention are, for example, stem cells derived from rodents such as mouse, rat, hamster, guinea pig and the like, Lagomorpha such as rabbit and the like, Ungulata such as swine, bovine, goat, horse, sheep and the like, Carnivora such as dog, cat and the like, primates such as human, monkey, Macaca mulatta, marmoset, orangutan, chimpanzee and the like. Preferred are stem cells derived from human.

1. Medium for Stem Cell Proliferation/Production Method of Medium for Stem Cell Proliferation The present invention provides a medium for stem cell proliferation containing a riboflavin derivative (hereinafter to be also referred to as the medium of the present invention) and a production method thereof.

The medium for stem cell proliferation of the present invention is generally prepared/produced as a complete medium by mixing a basal medium composed of an amino acid, a vitamin, a mineral, a buffering agent and the like with supplemental components such as protein and the like (to be also referred to as supplements). As one embodiment of the present invention, a complete medium obtained by mixing one or more supplements with the basal medium can be mentioned. When a plurality of supplements are used, they may adversely affect each other depending on the kind of the supplements, and are required to store separately (supplements 1 and 2, etc.). As another embodiment of the present invention, a complete medium obtained by mixing supplements 1 and 2 with the basal medium can be mentioned.

The medium for stem cell proliferation of the present invention (complete medium) preferably contains a riboflavin derivative, an amino acid, a vitamin, a mineral, a buffering agent, and one or more supplements.

The medium for stem cell proliferation of the present invention (complete medium) may be provided in the form a medium kit for stem cell proliferation, in which a basal medium containing amino acid, vitamin, mineral and buffering agent and one or more supplements are sealed in separate containers such as bottle and the like and are combined, and they are mixed when in use and used as a complete medium.

The basal medium to be used in the present invention characteristically contains a riboflavin derivative. Except that the riboflavin derivative is the essential component, the composition thereof is the same as that of media known per se that permit stem cell proliferation culture, such as DMEM, DMEM/F-12, EMEM, IMDM (Iscove's Modified Dulbecco's Medium), GMEM (Glasgow's MEM), RPMI-1640, α-MEM, Ham's Medium F-12, Ham's Medium F-10, Ham's Medium F12K, Medium 199, ATCC-CRCM30, DM-160, DM-201, BME, Fischer, McCoy's 5A, RITC80-7, MCDB105, MCDB107, MCDB131, MCDB153, MCDB201, NCTC109, NCTC135, Waymouth's MB752/1, CMRL-1066, Williams' medium E and Brinster's BMOC-3 Medium, and the basal media used for Essential 8 (Thermo Fisher SCIENTIFIC), ReproFF2 (ReproCELL Incorporated), mTeSR1 (STEMCELL Technologies), TeSR2 (STEMCELL Technologies), TeSR-E8 (STEMCELL Technologies), StemFit (registered trade mark) AK (Ajinomoto Co., Inc.) and the like, and can be prepared based on such composition. As a preferable basal medium, a medium generally used by adding RFV can be mentioned.

Examples of the riboflavin derivative used in the present invention include, but are not limited to, flavin mononucleotide (FMN), flavin adenine dinucleotide (FAD), riboflavin butyrate (e.g., riboflavin tetrabutyrate), salts thereof, hydrates thereof and the like. Hereinafter, unless particularly specified, FMN includes flavin mononucleotide, a salt thereof and a hydrate thereof, FAD includes flavin adenine dinucleotide, a salt thereof and a hydrate thereof, and RTB includes riboflavin butyrate (riboflavin tetrabutyrate), a salt thereof and a hydrate thereof. The riboflavin derivative used in the present invention is preferably FAD. Examples of the salt form include an acid addition salt, a salt with a base and the like, and a salt not showing cytotoxicity and acceptable as a pharmaceutical product is preferable. Examples of the acid forming such salt include inorganic acids such as hydrogen chloride, hydrogen bromide, sulfuric acid, phosphoric acid and the like, and organic acids such as acetic acid, lactic acid, citric acid, tartaric acid, maleic acid, fumaric acid, mesylic acid, monomethyl sulfate and the like. Examples of the base forming such salt include hydroxide or carbonate of a metal such as sodium, potassium, calcium and the like, inorganic bases such as ammonia and the like, organic base such as ethylenediamine, propylenediamine, ethanolamine, monoalkylethanolamine, dialkylethanolamine, diethanolamine, triethanolamine and the like. The above-mentioned salt may be a hydrate (hydrate salt). As FAD, flavin adenine dinucleotide disodium salt hydrate is preferably used. As FMN, riboflavin 5'-monophosphate sodium salt, riboflavin 5'-monophosphate sodium salt dihydrate (riboflavin 5'-phosphate sodium dihydrate) is preferably used.

Riboflavin derivatives (including salts thereof and hydrates thereof) are commercially available, and can also be prepared according to a known document.

In the present invention, the concentration of the riboflavin derivative in the basal medium (concentration converted to free form anhydrate in the case of salt and/or hydrate) is not particularly limited as long as degradation of the complete medium is suppressed. It is generally 5 nM to 500 µM, preferably 5 nM to 100 µM, particularly preferably 5 nM to 20 µM, in the medium for stem cell proliferation of the present invention (complete medium).

When the riboflavin derivative is FMN (concentration converted to free form anhydrate of FMN in the case of salt and/or hydrate), it is preferably 5 nM to 3 µM in the medium for stem cell proliferation of the present invention (complete medium); when the riboflavin derivative is FAD (converted to free form anhydrate of FAD in the case of salt and/or hydrate), it is preferably 5 nM to 20 µM in the medium for stem cell proliferation of the present invention (complete medium); when the riboflavin derivative is RTB (converted to free form anhydrate of RTB in the case of salt and/or hydrate), it is preferably 5 nM to 0.5 µM in the medium for stem cell proliferation of the present invention (complete medium).

In the case where the basal medium in the medium of the present invention contains a compound containing iron ($Fe^{2+}$) (e.g., ferrous sulfate heptahydrate) at 0.083 to 0.125 mg/L (preferably about 0.104 mg/L), and a compound containing zinc ($Zn^{2+}$) (e.g., zinc sulfate heptahydrate) at 0.086 to 0.13 mg/L (preferably about 0.108 mg/L), when the riboflavin derivative is FMN (concentration converted to free form anhydrate of FMN in the case of salt and/or hydrate), it is particularly preferably 5 nM to 2.57 µM in the medium for stem cell proliferation of the present invention (complete medium); when the riboflavin derivative is FAD (converted to free form anhydrate of FAD in the case of salt and/or hydrate), it is particularly preferably 5 nM to 15.2 µM in the medium for stem cell proliferation of the present invention (complete medium); when the riboflavin derivative is RTB (converted to free form anhydrate of RTB in the case of salt and/or hydrate), it is particularly preferably 5 nM to 0.47 µM in the medium for stem cell proliferation of the present invention (complete medium).

In the case where the basal medium in the medium of the present invention contains a compound containing iron ($Fe^{2+}$) (e.g., ferrous sulfate heptahydrate) at 0.332 to 0.5 mg/L (preferably about 0.417 mg/L), and a compound containing zinc ($Zn^{2+}$) (e.g., zinc sulfate heptahydrate) at 0.344 to 0.52 mg/L (preferably about 0.432 mg/L), when the riboflavin derivative is FMN (concentration converted to free form anhydrate of FMN in the case of salt and/or hydrate), it is particularly preferably 5 nM to 0.47 µM in the medium for stem cell proliferation of the present invention (complete medium); when the riboflavin derivative is FAD (converted to free form anhydrate of FAD in the case of salt and/or hydrate), it is particularly preferably 5 nM to 2.57 µM in the medium for stem cell proliferation of the present invention (complete medium); when the riboflavin derivative is RTB (converted to free form anhydrate of RTB in the case of salt and/or hydrate), it is particularly preferably 5 nM to 0.47 µM in the medium for stem cell proliferation of the present invention (complete medium).

Examples of the amino acid contained in the basal medium include glycine, L-alanine, L-arginine, L-asparagine (e.g., L-asparagine (monohydrate)), L-aspartic acid, L-cysteine, L-cystine (e.g., L-cystine dihydrochloride), L-glutamic acid, L-glutamine, L-histidine, L-isoleucine, L-leucine, L-lysine (e.g., L-lysine hydrochloride), L-methionine, L-phenylalanine, L-proline, L-serine, L-threonine, L-tryptophan, L-tyrosine and L-valine. Various amino acids are each preferably contained in the concentration range known per se.

The content of the amino acid contained in the basal medium is, for example, about 1 mg to 100 g per 1 L of the basal medium.

Examples of the vitamin contained in the basal medium include inositol (e.g., myo-inositol), choline (e.g., choline chloride), vitamin A, vitamin B1 (thiamine (e.g., thiamine hydrochloride)), vitamin B3, vitamin B4, vitamin B5 (pantothenic acid (e.g., D-calcium pantothenate)), vitamin B6 (pyridoxine (e.g., pyridoxine hydrochloride)), vitamin B7 (biotin (e.g., D-biotin)), vitamin B12, vitamin B13, vitamin B15, vitamin B17, vitamin Bh, vitamin Bt, vitamin Bx, vitamin D, vitamin E, vitamin F, vitamin K, vitamin M (folic acid), vitamin P and nicotinamide. Various vitamins are each preferably contained within a concentration range known per se. The basal medium used in the present invention does not contain riboflavin, or even when it contains, the concentration thereof is generally not more than 6 µM, preferably not more than 0.6 µM, more preferably not more than 0.6 nM, in the complete medium. That is, the concentration of riboflavin in the basal medium is 0 to 6 µM, preferably 0 to 0.6 µM, more preferably 0 to 0.6 nM. Particularly preferably, the basal medium of the present invention does not contain riboflavin.

The concentration of vitamin contained in the basal medium is, for example, about 0.0001 to 100 mg per 1 L of the basal medium.

As the mineral contained in the basal medium, calcium chloride (e.g., calcium chloride (anhydrous)), copper sulfate (e.g., copper sulfate pentahydrate), iron (III) nitrate (e.g., iron (III) nitrate nonahydrate), iron sulfate (e.g., iron (II) sulfate heptahydrate), magnesium chloride (e.g., magnesium chloride hexahydrate), magnesium sulfate (e.g., magnesium sulfate (anhydrous)), potassium chloride, sodium hydrogen carbonate, sodium chloride, disodium hydrogen phosphate, sodium dihydrogen phosphate (e.g., sodium dihydrogen phosphate (anhydrous)) and zinc sulfate (e.g., zinc sulfate heptahydrate) can be mentioned. Various minerals can be contained within a concentration range known per se.

The content of the mineral in the basal medium is, for example, about 0.0001 to 10000 mg per 1 L of the basal medium.

The medium of the present invention (preferably basal medium) preferably contains at least iron and/or zinc (e.g., iron sulfate or hydrate thereof (e.g., iron (II) sulfate heptahydrate) and/or zinc sulfate or hydrate thereof (e.g., zinc sulfate heptahydrate)).

The content of iron sulfate or hydrate thereof in the medium of the present invention is preferably 5 to 500 mol %, more preferably 10 to 150 mol %, further preferably 20 to 30 mol %, of the content of iron sulfate or hydrate thereof in DMEM/F-12.

The content of zinc sulfate or hydrate thereof in the medium of the present invention is preferably 5 to 500 mol %, more preferably 10 to 150 mol %, further preferably 20 to 30 mol %, of the content of zinc sulfate or hydrate thereof in DMEM/F-12.

The content of iron sulfate or hydrate thereof in the medium of the present invention is preferably 0.021 to 2.085 mg, more preferably 0.042 to 0.626 mg, further preferably 0.083 to 0.125 mg, for iron (II) sulfate heptahydrate, per 1 L of the basal medium.

The content of zinc sulfate or hydrate thereof in the medium of the present invention is preferably 0.022 to 2.160 mg, more preferably 0.043 to 0.648 mg, further preferably 0.086 to 0.130 mg, for zinc sulfate heptahydrate, per 1 L of the basal medium.

Examples of the buffering agent contained in the basal medium include phosphate buffered saline (PBS), citrate buffer, HEPES and the like.

The content of the buffering agent in the basal medium is, for example, about 0.001 to 10000 mg per 1 L of the basal medium.

The basal medium used in the present invention can contain an additive known per se. Examples of the additive include saccharides (e.g., glucose etc.), organic acids (e.g., pyruvic acid (e.g., sodium pyruvate), lactic acid etc.), reducing agents (e.g., 2-mercaptoethanol etc.), steroids (e.g., 3-estradiol, progesterone etc.), antibiotics (e.g., streptomycin, penicillin, gentamicin etc.), purine derivatives (e.g., hypoxanthine), thioctic acids (e.g., DL-lipoic acid), fatty acids (e.g., linoleic acid), pH indicators (e.g., phenol red), polyamines (e.g., 1,4-butanediamine dihydrochloride), pyrimidinedeoxynucleotides (e.g., thymidine) and the like.

In addition, additives that have been conventionally used for culturing stem cells can be contained as appropriate. The additive is preferably contained within a concentration range known per se.

Examples of the component contained in the supplement of the present invention include proteins such as insulin, bFGF, transferrin, TGF-β and the like, minerals such as selenium, sodium hydrogen carbonate and the like, and vitamins such as L-ascorbic acid and the like. Supplements that are not desired to coexist are prepared separately. That is, in the present invention, supplements are provided as supplement 1, and supplement 1 and supplement 2 as necessary. In the present invention, a supplement or a commercially available product can be used as a supplement. As the supplement in the present invention, those previously reported or commercially available ones can be used. For example, a supplement solution of Essential 8 (Thermo Fisher SCIENTIFIC) and a supplement solution of TeSR-E8 (STEMCELL Technologies) can be used.

In the medium of the present invention, the amount of the supplement is, for example, about 1 to 50 parts by weight per 100 parts by weight of the basal medium.

The medium to be used in the present invention may contain a serum. The serum is not particularly limited as long as it is derived from an animal and does not inhibit the growth of stem cells. Preferred is a mammal-derived serum (e.g., fetal bovine serum, human serum etc.). The concentration of the serum may be any as long as it is within a concentration range known per se. However, a lower content of serum is more preferable, and the absence of serum is most preferable, since it is known that serum components also contain a differentiation factor of human ES cell, and the like, and the culture results may be inconsistent due to a difference between serum lots. Furthermore, when a stem cell after culture is used for medical purposes, a xeno-derived component may become an infection source of blood-mediated pathogen or a xenoantigen. Therefore, the absence of serum is preferable. When serum is not contained, a replacement additive of serum (e.g., Knockout Serum Replacement (KSR) (Invitrogen), Chemically-defined Lipid concentrated (Gibco), Glutamax (Gibco), B-27 Supplement etc.) may also be used. These components are generally provided as supplements apart from the basal medium.

2. Stabilizer of Medium for Stem Cell Proliferation/Method for Stabilizing Medium for Stem Cell Proliferation The medium for stem cell proliferation is generally composed of a basal medium and a supplement (one or more supplements), and is prepared as a liquid complete medium by mixing at the time of use. The complete medium after storage shows lower performance in cell proliferation, but degradation of the medium after storage can be prevented by adding a riboflavin derivative to the medium. In the present specification, the "degradation" of the complete medium after storage means that the degree of cell proliferation is lower than that when the cells are cultured in the medium before storage (e.g., immediately after preparation). In the method for stabilizing a medium for stem cell proliferation characterized by addition of a riboflavin derivative (hereinafter to be also referred to as the stabilization method of the present invention), the riboflavin derivative to be added includes those similar to the riboflavin derivative used for the medium for stem cell proliferation in the above-mentioned 1. The riboflavin derivative may be added to the complete medium or the basal medium, and is preferably added to the basal medium. The amount of the riboflavin derivative to be added in the stabilizing method of the present invention is not particularly limited as long as degradation due to storage of the medium for stem cell proliferation in a liquid state can be suppressed. It is generally added to the basal medium at 6 nM to 16 μM, preferably 6 nM to 3 μM, more preferably 6 nM to 0.6 μM. The amount of the riboflavin derivative to be added in the stabilizing method of the present invention is such an amount that achieves 5 nM to 500 μM, preferably 5 nM to 100 μM, particularly preferably 5 nM to 20 μM, in the medium for stem cell proliferation (complete medium). For facilitated addition to the basal medium or complete medium, a stabilizer for a medium for stem cell proliferation containing a riboflavin derivative at a predetermined concentration (hereinafter to be also referred to as the stabilizer of the present invention) may be prepared in advance. The stabilizer in the present invention may or may not contain other components as long as it contains a riboflavin derivative as an active ingredient. In view of ease of handling, storage stability and the like, as well as use by addition to a medium, it may contain various additives. While those known per se are used as the various additives, they can also be formulated together with one or more kinds of medium constituent components.

The dosage form of the stabilizer of the present invention is not particularly limited, and may be in the form of a solution (including dosage forms such as suspension, emulsion and the like), a solid (including dosage forms such as powder and the like) or a semi-solid (including dosage forms such as gel and the like). The stabilizer of the present invention is preferably in the form of a solution because addition to a liquid medium is easy. The solid and semi-solid stabilizers of the present invention are preferable from the viewpoints of ease of handling, storage stability and the like. The solid and semi-solid stabilizers of the present invention can be added to the medium as they are, or can also be used after dissolving as necessary before addition to the medium.

The form of the basal medium and supplement of the present invention is not particularly limited, and they may be in the form of a solution (including suspension, emulsion and the like), a solid (including powder, etc.) or a semi-solid (including gel and the like). The basal medium of the present invention in the form of a solution is a solution-like medium obtained by adding a desired medium constituent component in addition to the riboflavin derivative. When the supplement is a solution, they can be directly mixed and used as a complete medium for culturing stem cells. When the supplement is solid or semi-solid, a solution of the supplement may be prepared in advance and they may be mixed, or the supplement may be directly dissolved in the basal medium in the form of a solution. When the basal medium of the present invention is solid or semi-solid, it contains desired medium constituent components (1 to 2 or more, preferably all) in addition to the riboflavin derivative, and is dissolved in purified water and the like when in use. When the supplement is a solution, they can be directly mixed and used as a complete medium for culturing stem cells. When the supplement is solid or semi-solid, a solution of the supplement may be prepared in advance and they may be mixed, or the supplement may be directly dissolved in the basal medium in the form of a solution. Where necessary, the pH can be adjusted and the basal medium can be used for cell culture. All these embodiments are within the scope of the medium for stem cell proliferation of the present invention.

The present invention provides a method of culturing stem cells (hereinafter to be also referred to as the culture method of the present invention).

3. Culture Method of the Present Invention

The culture method of the present invention includes a step of cultivating stem cells (preferably, iPS cells) in the medium of the present invention.

While a culture container to be used for the culture of stem cell is not particularly limited as long as stem cells can be cultured, a flask, tissue culture flask, dish, petri dish, tissue culture dish, multidish, microplate, microwell plate, multiplate, multiwell plate, microslide, chamber slide, Schale, tube, tray, culture bag and roller bottle can be mentioned.

The culture container may be cell adhesive or cell non-adhesive, and is appropriately selected according to the object. A cell adhesive culture container may be coated with any cell supporting substrate such as extracellular matrix (ECM) and the like, in an attempt to improve the adhesiveness of the culture container surface to a cell. The cell supporting substrate may be any substance aiming at adhesion of stem cell or feeder cell (when used).

Other culture conditions can be appropriately determined. For example, while the culture temperature is not particularly limited, it can be about 30 to 40° C., preferably about 37° C. The $CO_2$ concentration can be about 1 to 10%, preferably about 2 to 5%. The oxygen partial pressure can be 1 to 10%.

Stem cells can be proliferated efficiently by culturing them in the medium of the present invention, and therefore, the present invention can provide an efficient production method of stem cells.

Other features of the invention will become apparent in the course of the following descriptions of exemplary embodiments which are given for illustration of the invention and are not intended to be limiting thereof.

EXAMPLES

Materials and Methods

In this Example, the storage stability of Modified DMEM/F-12 medium, which is DMEM/F-12 medium with modified components, was evaluated using induced pluripotent stem cells (iPS cells).

The composition of Modified DMEM/F-12 medium is shown in Table 1. A medium having the composition of Table 1 except for FMN is Modified DMEM/F-12 (FMN−). Table 2 shows excerpts of differences in the medium composition.

TABLE 1

| starting material | [mg/L] | starting material | [mg/L] |
|---|---|---|---|
| glycine | 18.75 | thiamine hydrochloride | 2.17 |
| L-alanine | 4.45 | vitamin B12 | 0.68 |
| L-glutamine | 365 | myo-inositol | 12.6 |
| L-arginine | 122 | calcium chloride (anhydrous) | 116.6 |
| L-asparagine (monohydrate) | 7.5 | copper sulfate pentahydrate | 0.0013 |
| L-aspartic acid | 6.65 | iron (III) nitrate nonahydrate | 0 |
| L-cysteine hydrochloride monohydrate | 17.56 | iron (II) sulfate heptahydrate | 0.104 (25 mol %) |
| L-cystine dihydrochloride | 31.3 | magnesium chloride hexahydrate | 61.2 |
| L-glutamic acid | 7.35 | magnesium sulfate (anhydrous) | 48.84 |
| L-histidine | 23.3 | potassium chloride | 311.8 |
| L-isoleucine | 54.47 | sodium hydrogen carbonate | 1200 |
| L-leucine | 59.05 | sodium chloride | 6996 |
| L-lysine hydrochloride | 91.25 | disodium hydrogen phosphate | 71.02 |
| L-methionine | 17.24 | sodium dihydrogen phosphate (anhydrous) | 54.3 |
| L-phenylalanine | 35.48 | zinc sulfate heptahydrate | 0.108 (25 mol %) |
| L-proline | 17.25 | glucose | 3150 |
| L-serine | 26.25 | HEPES | 3574.5 |
| L-threonine | 53.45 | hypoxanthine | 2.1 |
| L-tryptophan | 9.02 | DL-lipoic acid | 0.105 |
| L-tyrosine | 38.73 | linoleic acid | 0.042 |
| L-valine | 52.85 | Phenol red | 8.1 |
| D-biotin | 0.0035 | 1,4-butanediamine dihydrochloride | 0.081 |
| choline chloride | 8.98 | sodium pyruvate | 55 |
| D-calcium pantothenate | 2.25 | thymidine | 0.375 |
| folic acid | 2.65 | FMN | 0.056 |
| nicotinamide | 2.03 | | |
| pyridoxine hydrochloride | 2.0 | | |

TABLE 2

| | | DMEM/F-12 | Modified DMEM/F-12 | Modified DMEM/F-12 (FMN-) |
|---|---|---|---|---|
| iron (III) nitrate nonahydrate | concentration [mg/L] | 0.05 mg/L | 0 mg/L | 0 mg/L |
| | relative concentration [mol % vs DMEM/F-12] | 100 | 0 | 0 |
| iron (II) sulfate heptahydrate | concentration [mg/L] | 0.417 mg/L | 0.104 mg/L | 0.104 mg/L |
| | relative concentration [mol % vs DMEM/F-12] | 100 | 25 | 25 |
| zinc sulfate heptahydrate | concentration [mg/L] | 0.432 mg/L | 0.108 mg/L | 0.108 mg/L |
| | relative concentration [mol % vs DMEM/F-12] | 100 | 25 | 25 |
| RFV | concentration [mg/L] | 0.219 mg/L | 0 mg/L | 0 mg/L |
| | relative concentration [mol % vs DMEM/F-12] | 100 | 0 | 0 |
| FMN | concentration [mg/L] | 0 mg/L | 0.056 mg/L | 0 mg/L |
| | relative concentration [mol % vs DMEM/F-12 as RFV] | 0 | 20 (as RFV) | 0 |

The following 4 points were modified in the composition of DMEM/F-12.

(i) RFV was changed to flavin mononucleotide (FMN) Na salt (Riboflavin 5'-Monophosphate Sodium Salt (Tokyo Kasei Kogyo Co., Ltd., R0023, hereinafter the same)) which is a riboflavin derivative, and the concentration was reduced to 20 mol %.

(ii) $Fe^{3+}$ (iron (III) nitrate nonahydrate) was set to 0 mol %.

(iii) $Fe^{2+}$ (iron (II) sulfate heptahydrate) was reduced to 25 mol %.

(iv) The content of $Zn^{2+}$ (zinc sulfate heptahydrate) was reduced to 25 mol %.

201B7 strain purchased from iPS Academia Japan, Inc. was used as the iPS cell. Cell culture was performed using a culture vessel coated with Matrigel (Nippon Becton, Dickinson and Company: 354277) or iMatrix-511 (Nippi. Inc.: 892002) as an extracellular matrix under conditions of 5% $CO_2$/37° C.

Modified DMEM/F-12 was mixed with each supplement of Essential 8 (Thermo Fisher SCIENTIFIC: A1517001), TeSR-E8 (STEMCELL Technologies: #05940), TeSR2 (STEMCELL Technologies: #05860) to prepare a complete medium. The medium was stored in a refrigerator with a glass door under non-light-shielding (fluorescent light irradiation time: 10 hr/day) and then used for culture, based on which the storage stability of the medium was studied.

In each of the following Examples, "Essential 8 supplement" is a supplement of Essential 8 (Thermo Fisher SCIENTIFIC: A1517001), "TeSR-E8 supplement" is a supplement of TeSR-E8 (STEMCELL Technologies: #05940), and "TeSR2 supplement" is a supplement of TeSR2 (STEMCELL Technologies: #05860).

Example 1: Study of Effectiveness of RFV During iPS Cell Culture

Whether RFV is an essential component during iPS cell culture was studied. A complete medium was prepared by mixing the basal medium (Solution A: Modified DMEM/F-12 (FMN−)) and Essential 8 supplement (Solution B). Media were prepared by adding RFV to the complete medium to final concentrations of 0.00, 0.0176, 0.044, 0.088, 0.176 mg/L (No. 1 to No. 5 in Table 3). Along therewith, to grasp the influence of the reduced mineral components, media supplemented with $Fe^{2+}$ and $Zn^{2+}$ at 100 mol % were also prepared (No. 6 to No. 10 in Table 3).

After preparing the medium, a 12-well plate coated with Matrigel was prepared, and 10,000 cells per well were seeded in a single cell state. On the day when the cells were seeded, the evaluation was performed using the medium prepared above. The culture period was set to 7 days, and the cell confluency was measured as an index of cell proliferation using IncuCyte Zoom (Essen Bioscience) on day 7 from the start of the culture. At the time of seeding, a medium supplemented with Y-27632 (Wako Pure Chemical Industries, Ltd.: 036-24023) at a final concentration of 10 μM was used. In the evaluation from the following day, the cells were cultured in a medium not supplemented with Y-27632.

Figure 2:
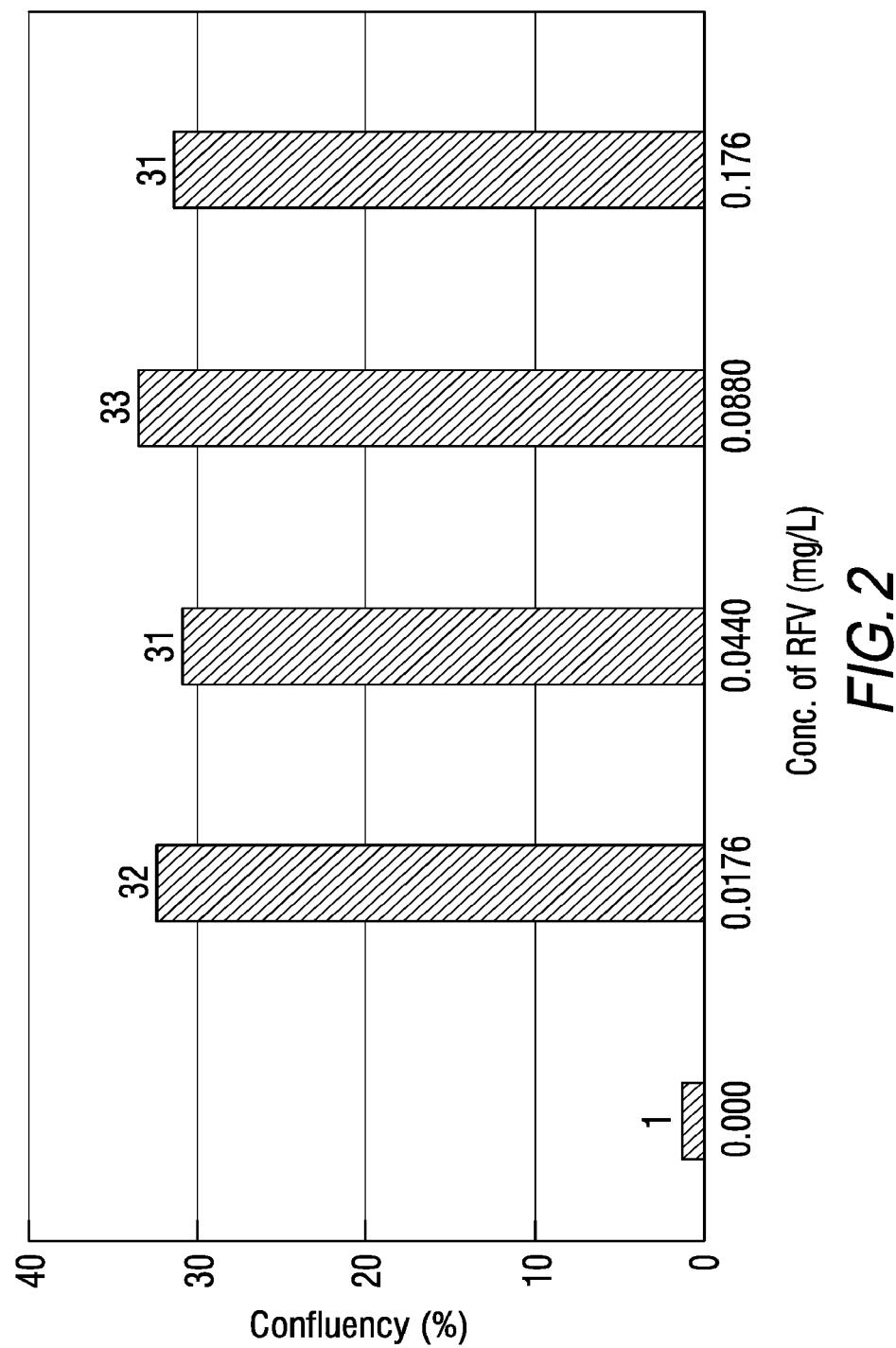
FIG. 2 is a graph showing the study results of the effectiveness of RFV during iPS cell culture (when $Fe^{2+}$ content and $Zn^{2+}$ content were both 100 mol % of the basal medium). The vertical axis shows the cell confluency (%) and the horizontal axis shows the RFV concentration.

The results are shown in FIGS. 1 and 2. At any $Fe^{2+}$ and $Zn^{2+}$ concentrations, the cells were killed at RFV 0.00 mg/L. It was shown that RFV is essential for cell culture.

TABLE 3

| No. | Added RFV concentration [mg/L] | [mol % vs DMEM/F-12] | $Fe^{2+}$ content percentage [mol %] | $Zn^{2+}$ content percentage [mol %] | Solution A | Solution B |
|---|---|---|---|---|---|---|
| 1 | 0.00 | 0.0 | 25 | 25 | Modified DMEM/F-12 | Essential 8 |
| 2 | 0.0176 | 8.0 | | | | |
| 3 | 0.0440 | 20 | | | | |

TABLE 3-continued

| No. | Added RFV concentration [mg/L] | [mol % vs DMEM/F-12] | $Fe^{2+}$ content percentage [mol %] | $Zn^{2+}$ content percentage [mol %] | Solution A | Solution B |
|---|---|---|---|---|---|---|
| 4 | 0.0880 | 40 | | | | (FMN−) |
| 5 | 0.176 | 80 | | | | |
| 6 | 0.00 | 0.0 | 100 | 100 | | |
| 7 | 0.0176 | 8.0 | | | | |
| 8 | 0.0440 | 20 | | | | |
| 9 | 0.0880 | 40 | | | | |
| 10 | 0.176 | 80 | | | | |

Example 2: Study of Effect of Modified DMEM/F-12 Medium

The effect of Modified DMEM/F-12 which is DMEM/F-12 with modification was studied. A complete medium composed of a basal medium (Solution A) and a supplement (Essential 8 supplement (Solution B) or TeSR-E8 supplement (Solution B, Solution C)) was prepared by combining DMEM/F-12 and Modified DMEM/F-12 as shown below (Table 4). Each medium was refrigerated under non-light-shielding for 0, 2, and 5 weeks and then the proliferation ability of iPS cells was measured.

TABLE 4

| No. | Solution A | $Fe^{2+}$ content percentage [mol %] | $Zn^{2+}$ content percentage [mol %] | Solution B | Solution C |
|---|---|---|---|---|---|
| 1 | DMEM/F-12 | 25 | 25 | Essential 8 | — |
| 2 | Modified DMEM/F-12 | | | Essential 8 | — |
| 3 | DMEM/F-12 | | | TeSR-E8 | TeSR-E8 |
| 4 | Modified DMEM/F-12 | | | TeSR-E8 | TeSR-E8 |

A 12-well plate coated with Matrigel was prepared, 10,000 cells per well were seeded in a single cell state and the proliferation ability was evaluated. On the day when the cells were seeded, the evaluation was started using the medium prepared above. The culture period was set to 7 days, and the cell confluency was measured using IncuCyte Zoom on day 7 from the start of the culture. At the time of seeding, a medium supplemented with Y-27632 at a final concentration of 10 μM was used. In the evaluation from the following day, the cells were cultured in a medium not supplemented with Y-27632.

Figure 3A:
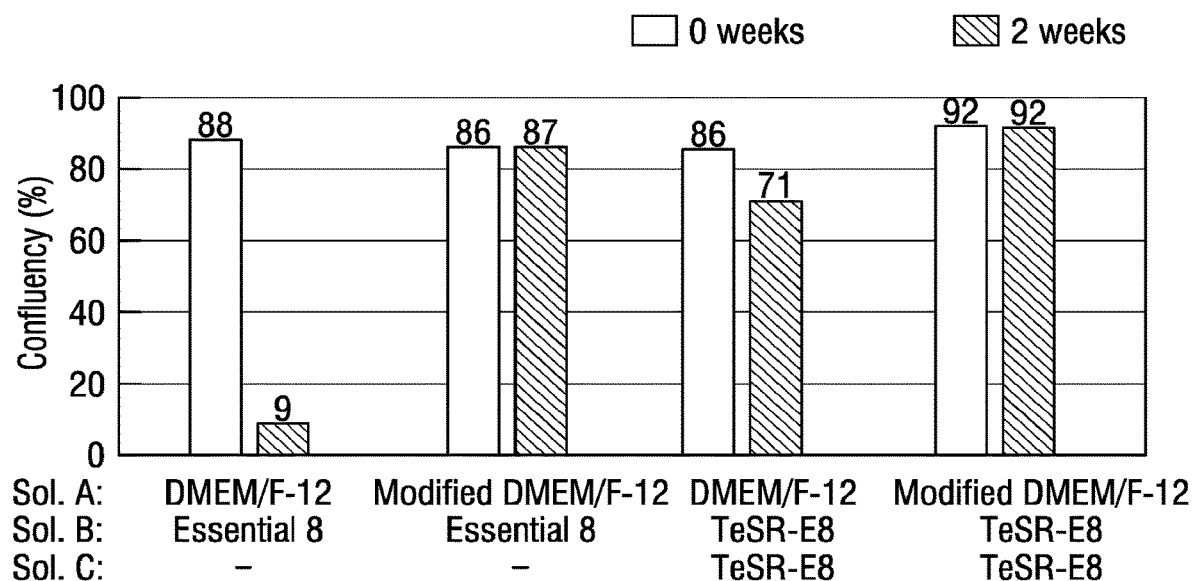
FIG. 3 depicts graphs showing the measurement results of cell proliferation ability (cell confluency) when iPS cells were cultured using various media stored in a refrigerator (2-8° C., 2 weeks or 5 weeks). The upper graph shows the results of the medium refrigerated for 2 weeks, and the lower graph shows the results of the medium refrigerated for 5 weeks. Each medium uses DMEM/F-12 containing RFV or Modified DMEM/F-12 containing FMN instead of RFV as a basal medium (Solution A) and the supplement of Essential 8 (Solution B only) or the supplements of TeSR-E8 (Solution B and Solution C) as the supplement(s) (Solution B and Solution C).
Figure 3B:
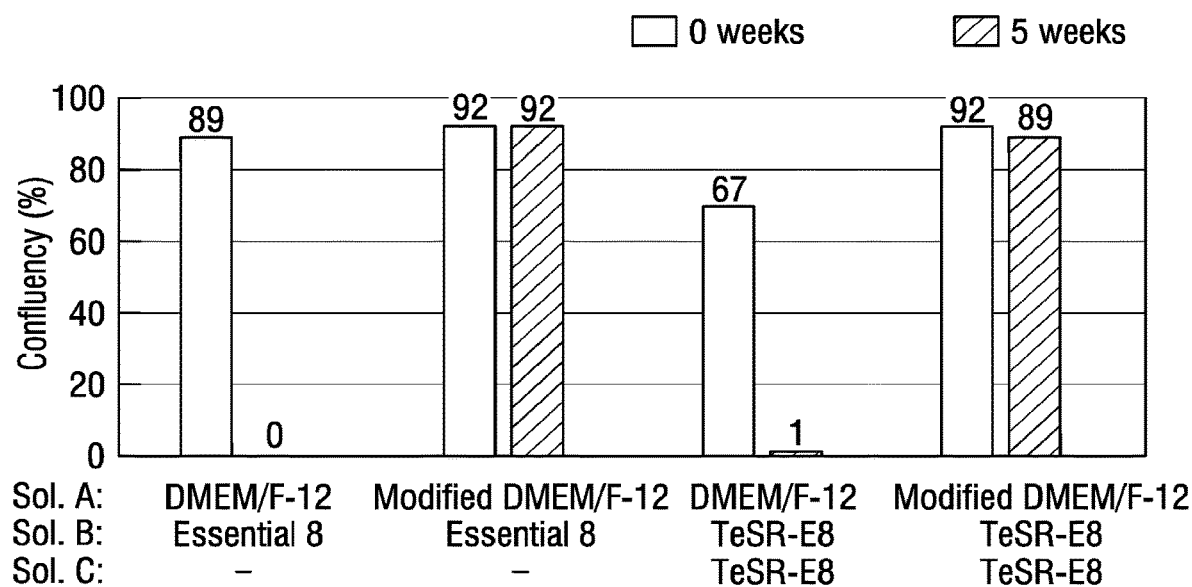

FIG. 3 shows proliferation ability study results after storage for 2 weeks (upper graph of FIG. 3) or 5 weeks (lower graph of FIG. 3). The proliferation ability study results reveal that the stability of medium can be maintained even after storage for 5 weeks when the basal medium was Modified DMEM/F-12.

Example 3: Study of Influence of Fe, Zn, RFV on Storage Stability

To what extent $Fe^{2+}$, $Zn^{2+}$ and RFV contribute to the storage stability of the medium was studied. Complete media were respectively prepared by adding each component to Modified DMEM/F-12 (FMN−) (Table 5). Each medium was refrigerated under non-light-shielding for 0 and 2 weeks and then the proliferation ability of iPS cells was studied.

TABLE 5

| | | | studied composition*[1] of medium | | |
|---|---|---|---|---|---|
| No. | Solution A | Solution B | $Fe^{2+}$ content percentage [mol %] *[2] | $Zn^{2+}$ content percentage [mol %] *[3] | RFV or RFV derivative addition concentration [mol %] *[4] |
| 1 | DMEM/F-12 | Essential 8 | 100 | 100 | RFV: 100 |
| 2 | | | 25 | 25 | FMN: 20 |
| 3 | Modified | | 100 | 25 | FMN: 20 |
| 4 | DMEM/F-12 | | 25 | 100 | FMN: 20 |
| 5 | (FMN-) | | 25 | 25 | FMN: 20, RFV: 80 |

*[1] In the above-mentioned Nos. 2 to 5, RFV derivative (FMN: Riboflavin 5'-Monophosphate Sodium Salt) was added to Modified DMEM/F-12 (FMN-) to a predetermined concentration.
*[2] In No. 3, iron (II) sulfate heptahydrate was added as $Fe^{2+}$ to Modified DMEM/F-12 (FMN-). The mol % is a mol concentration relative to DMEM/F-12, and 100 mol % of iron (II) sulfate heptahydrate is 0.417 mg/L (Table 2).
*[3] In No. 4, zinc sulfate heptahydrate was added as $Zn^{2+}$ to Modified DMEM/F-12 (FMN-) The mol % is a mol concentration relative to DMEM/F-12, and 100 mol % of zinc sulfate heptahydrate is 0.432 mg/L (Table 2).
*[4] In No. 5, RFV was added to Modified DMEM/F-12 (FMN-) in addition to the RFV derivative. The mol % is a mol concentration relative to DMEM/F-12, and 80 mol % of RFV is 0.176 mg/L (0.58 μM) (Table 2).

A 12-well plate coated with Matrigel was prepared, 10,000 cells per well were seeded in a single cell state. On the day when the cells were seeded, the evaluation was performed using the medium prepared above. The culture period was set to 7 days, and the cell confluency was measured using IncuCyte Zoom on day 7 from the start of the culture. At the time of seeding, a medium supplemented with Y-27632 at a final concentration of 10 μM was used. In the evaluation from the following day, the cells were cultured in a medium not supplemented with Y-27632.

Figure 4:
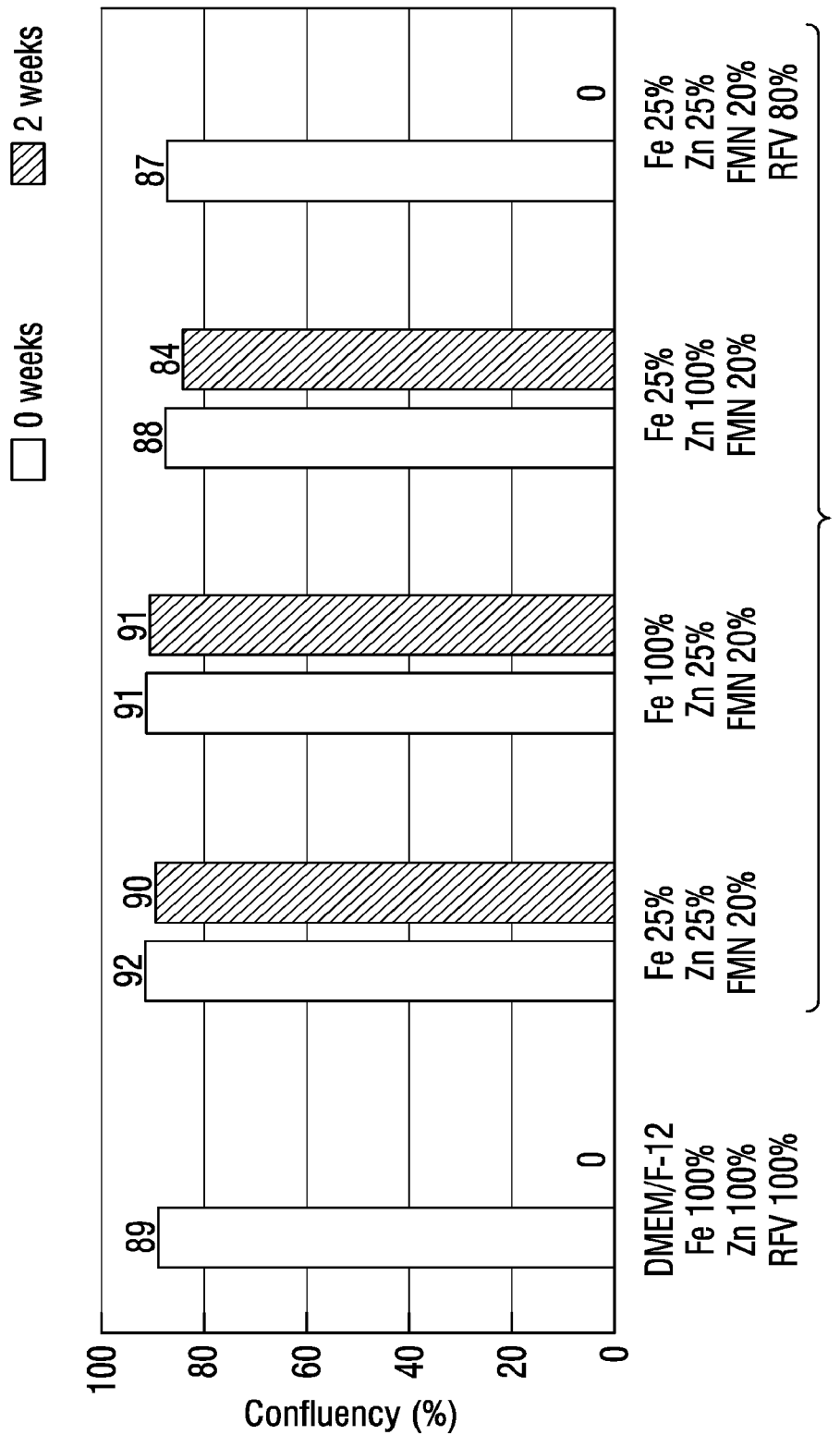
FIG. 4 is a graph showing the study results of the degree of contribution of $Fe^{2+}$, $Zn^{2+}$ and riboflavin to the storage stability of the medium. The cell proliferation ability (cell confluency) when iPS cells were cultured using various media refrigerated for 2 weeks was studied.

The proliferation ability study results are shown in FIG. 4. In the medium containing RFV, cells could not grow after storage for 2 weeks. Thus, the presence of riboflavin was considered as a cause of low storage stability. On the other hand, in this experiment, it was confirmed that $Fe^{2+}$ and $Zn^{2+}$ do not contribute to lowering of storage stability of the medium.

Example 4: Evaluation of iPS Cell Culture in L-15 Medium Using FMN

As a medium containing FMN instead of RFV, L-15 medium is recited which is commercially available for the proliferation of cells that proliferate rapidly such as tumor cell and the like. Whether this medium can be used as a medium for stem cells was studied. A complete medium was prepared using L-15 (Wako Pure Chemical Industries, Ltd.: 128-06075) as the basal medium and Essential 8 supplement as the supplement, and immediately after the preparation, the proliferation ability of iPS cell was studied. A 6-well plate coated with Matrigel or iMatrix-511 was prepared, 13,000 cells per well were seeded in a single cell state. On the day when the cells were seeded, the evaluation was performed using the medium prepared above. The culture period was set to 7 days, and the cell confluency was measured using IncuCyte Zoom on day 7 from the start of the culture. At the time of seeding, a medium supplemented with Y-27632 at a final concentration of 10 μM was used. In the evaluation from the following day, the cells were cultured in a medium not supplemented with Y-27632.

Figure 5A:
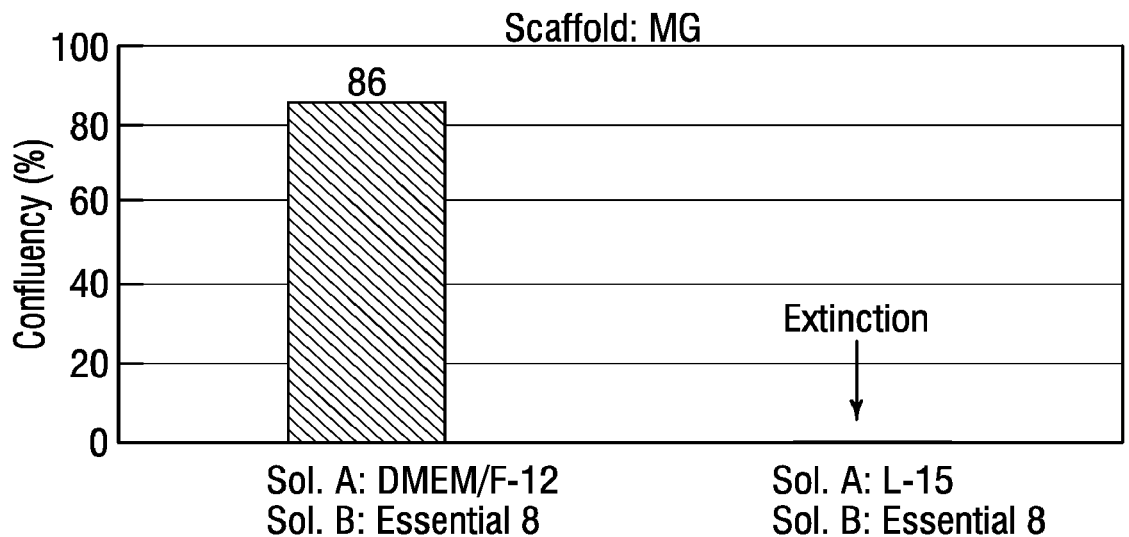
FIG. 5 depicts graphs showing the study results of cell proliferation ability when iPS cells were cultured using a commercially available L-15 medium (medium containing FMN). A complete medium was prepared using L-15 as a basal medium (Solution A) and supplement of Essential 8 as the supplement (Solution B), and the proliferation ability (cell confluency) of iPS cells was studied on the day of preparation. The upper graph shows the results when Matrigel was used as the scaffold, and the lower graph shows the results when iMatrix-511 was used as the scaffold. As a positive control, DMEM/F-12 was used as the basal medium (Solution A).
Figure 5B:
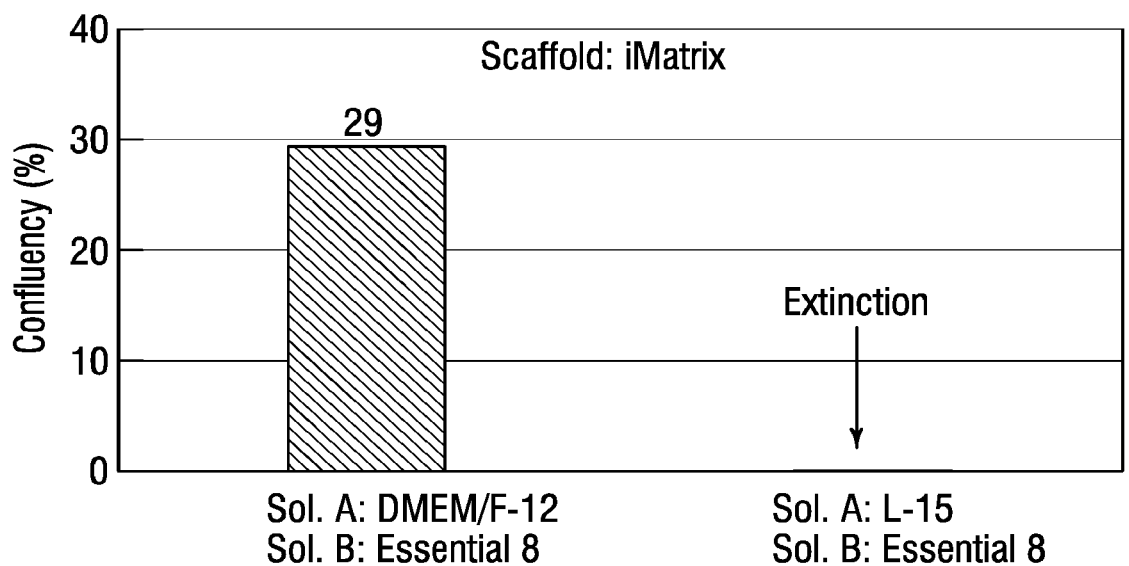

The results of Matrigel culture are shown in the upper graph of FIG. 5, and the results of iMatrix-511 culture are shown in the lower graph of FIG. 5. In both cultures, iPS cell could not be cultured regardless of the presence or absence of storage.

Example 5: Study of Effective Concentration of RFV Derivative FMN, FAD and RTB

The effectiveness of FAD and RTB, which are RFV derivatives, was studied, and the effective concentration ranges of FMN, FAD and RTB were studied. A complete medium was prepared using Modified DMEM/F-12 (FMN-) as the basal medium and Essential 8 or TeSR2 supplement as the supplement. RFV, FMN (Riboflavin 5'-Monophosphate Sodium Salt), FAD (Flavin Adenine Dinucleotide Disodium Salt Hydrate (Tokyo Chemical m Industry Co., Ltd., F0014, hereinafter the same)) and RTB (Riboflavin Tetrabutyrate, Wako Pure Chemical Industries, Ltd., 185-00861) were each added to the complete medium at a final concentration of 0.47 to 15.2 μM (concentration converted to free form anhydrate in the case of salt and/or hydrate). A medium supplemented with $Fe^{2+}$ and $Zn^{2+}$ at 100 mol % was also prepared.

Each medium was refrigerated under non-light-shielding for 2 weeks and then the proliferation ability of iPS cells was studied. A 12-well plate coated with Matrigel was prepared, 10,000 cells per well were seeded in a single cell state. On the day when the cells were seeded, the evaluation was performed using the medium prepared above. The culture period was set to 7 days, and the cell confluency was measured using IncuCyte Zoom on day 7 from the start of the culture. At the time of seeding, a medium supplemented with Y-27632 at a final concentration of 10 μM was used. In the evaluation from the following day, the cells were cultured in a medium not supplemented with Y-27632.

Tables 6 and 7 show the culture results of the medium using Essential 8 supplement, and Tables 8 and 9 show the culture results of the medium using TeSR2 supplement. In any medium, FMN, FAD and RTB all showed higher storage stability than that of RFV. In addition, the concentration at which culturing was possible was higher for FAD than FMN and RTB. The storage stability was higher when the concentrations of $Fe^{2+}$ and $Zn^{2+}$ were lower.

TABLE 6

| RFV or RFV derivative concentration | 0.47 μM (80 mol % vs DMEM/F-12) | 1.52 μM (259 mol % vs DMEM/F-12) |
|---|---|---|
| RFV | X | X |
| FMN | ○ | X |

TABLE 6-continued

| RFV or RFV derivative concentration | 0.47 μM (80 mol % vs DMEM/F-12) | 1.52 μM (259 mol % vs DMEM/F-12) |
|---|---|---|
| FAD | ○ | ○ |
| RTB | ○ | X |

(X; not grown, ○; cell grown)
*$Fe^{2+}$ and $Zn^{2+}$ were 25 mol %
basal medium: Modified DMEM/F-12 (FMN-), supplement: Essential 8 supplement

TABLE 7

| RFV or RFV derivative concentration | 0.47 μM (80 mol % vs DMEM/F-12) | 1.52 μM (259 mol %vs DMEM/F-12) |
|---|---|---|
| RFV | X | X |
| FMN | ○ | X |
| FAD | ○ | X |
| RTB | ○ | X |

(X; not grown, ○; cell grown)
*$Fe^{2+}$ and $Zn^{2+}$ were 100 mol %
basal medium: Modified DMEM/F-12 (FMN-), supplement: Essential 8 supplement

TABLE 8

| RFV or RFV derivative concentration | 0.47 μM (80 mol % vs DMEM/F-12) | 2.57 μM (437 mol % vs DMEM/F-12) | 15.2 μM (2587 mol % vs DMEM/F-12) |
|---|---|---|---|
| RFV | ○ | X | X |
| FMN | ○ | ○ | X |
| FAD | ○ | ○ | ○ |
| RTB | ○ | X | X |

(X; not grown, ○; cell grown)
*$Fe^{2+}$ and $Zn^{2+}$ were 25 mol %
basal medium: Modified DMEM/F-12 (FMN-), supplement: TeSR2 supplement

TABLE 9

| RFV or RFV derivative concentration | 0.47 μM (80 mol % vs DMEM/F-12) | 2.57 μM (437 mol % vs DMEM/F-12) | 15.2 μM (2587 mol % vs DMEM/F-12) |
|---|---|---|---|
| RFV | ○ | X | X |
| FMN | ○ | X | X |
| FAD | ○ | — (not performed) | X |
| RTB | ○ | X | X |

(X; not grown, ○; cell grown)
*$Fe^{2+}$ and $Zn^{2+}$ were 100 mol %
basal medium: Modified DMEM/F-12 (FMN-), supplement: TeSR2 supplement Example 6: Study of Effective Concentration of RFV Derivative FAD To study the effective concentration range of FAD, which is an RFV derivative, the unperformed part of Example 5 was evaluated. A complete medium was prepared using Modified DMEM/F-12 (FMN-) as the basal medium and TeSR2 supplement as the supplement. FAD (Flavin Adenine Dinucleotide Disodium Salt Hydrate) was added to the complete medium at a final concentration of 0.47 to 15.2 μM. A medium supplemented with $Fe^{2+}$ and $Zn^{2+}$ at 100 mol % was prepared.

Each medium was refrigerated under non-light-shielding for 2 weeks and then the proliferation ability of iPS cells was studied. A 12-well plate coated with Matrigel was prepared, 10,000 cells per well were seeded in a single cell state. On the day when the cells were seeded, the evaluation was performed using the medium prepared above. The culture period was set to 7 days, and the cell confluency was measured using IncuCyte Zoom on day 7 from the start of the culture. At the time of seeding, a medium supplemented with Y-27632 at a final concentration of 10 μM was used. In the evaluation from the following day, the cells were cultured in a medium not supplemented with Y-27632.

The culture results are shown in Table 10. When $Fe^{2+}$ and $Zn^{2+}$ were 100 mol %, culture was possible at 0.47 to 2.57 μM.

TABLE 10

| RFV derivative concentration | 0.47 μM (80 mol % vs DMEM/F-12) | 2.57 μM (437 mol % vs DMEM/F-12) | 15.2 μM (2587 mol % vs DMEM/F-12) |
|---|---|---|---|
| FAD | ○ | ○ | X |

(X; not grown, ○; cell grown)
*$Fe^{2+}$ and $Zn^{2+}$ were 100 mol %
basal medium: Modified DMEM/F-12 (FMN-), supplement: TeSR2 supplement

INDUSTRIAL APPLICABILITY

According to the present invention, a medium for cell proliferation that can avoid lowering of performance in cell proliferation even when it is stored in a liquid as a complete medium can be provided. As a result, more cells, in particular, pluripotent stem cells such as ES cell, iPS cell and the like can be efficiently obtained, and a large amount of cells can be supplied for use in research, medicine, and the like.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than m as specifically described herein.

All patents and other references mentioned above are incorporated in full herein by this reference, the same as if set forth at length.

The invention claimed is:

1. A medium suitable for culturing ES or iPS cells comprising a riboflavin derivative but not comprising riboflavin,
    wherein the riboflavin derivative is at least one selected from the group consisting of flavin adenine dinucleotide (FAD), flavin mononucleotide (FMN), riboflavin tetrabutyrate (RTB), salts thereof, and hydrates thereof, with the proviso that:
    when the riboflavin derivative comprises FAD, a salt thereof, or a hydrate thereof, a concentration of said FAD, a salt thereof, or a hydrate thereof in the medium is 5 nM to 20 μM,
    when the riboflavin derivative comprises FMN, a salt thereof, or a hydrate thereof, a concentration of said FMN, a salt thereof, or a hydrate thereof in the medium is 5 nM to 3 μM, and
    when the riboflavin derivative comprises RTB, a salt thereof, or a hydrate thereof, a concentration of said RTB, a salt thereof, or a hydrate thereof in the medium is 5 nM to 0.5 μM; and wherein ES or iPS cells when cultured in said medium not containing riboflavin, which has been stored for a time and at a temperature sufficient to degrade the riboflavin in a medium, have a greater proliferative ability than ES or iPS cells cultured in the otherwise identical medium containing riboflavin that has been stored for the same period of time and at the same temperature; and wherein said time and at a temperature sufficient to degrade the riboflavin in the medium is 2 weeks at a temperature ranging from 2° C. to 8° C.; and/or wherein the riboflavin derivative comprises RTB, a salt thereof, or a hydrate thereof; and/or wherein said medium is more stable when stored for two weeks at 2° C. to 8° C. than an otherwise identical medium containing riboflavin instead of the riboflavin derivative, wherein stability is determined by an increased amount of proliferation of ES or iPS cells.

2. The medium of claim 1, wherein said time and at a temperature sufficient to degrade the medium containing riboflavin is 2 weeks at a temperature ranging from 2° C. to 8° C.

3. The medium of claim 1, wherein the riboflavin derivative comprises FAD, a salt thereof, or a hydrate thereof.

4. The medium of claim 1, wherein the riboflavin derivative comprises FMN, a salt thereof, or a hydrate thereof.

5. The medium of claim 1, wherein the riboflavin derivative comprises RTB, a salt thereof, or a hydrate thereof.

6. The medium of claim 1, further comprising a mixture of a basal medium comprising an amino acid, a vitamin, a mineral and a buffering agent and one or more supplements.

7. The medium of claim 1 that further comprises a compound containing Fe2+ in an amount ranging from 0.083 to 0.125 mg/L and a compound containing Zn2+ in an amount ranging from 0.086 to 0.13 mg/L.

8. The medium of claim 1 that is more stable when stored for two weeks at 2° C. to 8° C. than an otherwise identical medium containing riboflavin instead of the riboflavin derivative, wherein stability is determined by an increased amount of proliferation of ES or iPS cells.

9. A method for increasing storage stability of a riboflavin-containing medium suitable for culturing ES or iPS cells comprising:

replacing the riboflavin in said riboflavin-containing medium with a riboflavin derivative to obtain a modified medium not containing riboflavin;

wherein the riboflavin derivative is at least one selected from the group consisting of flavin adenine dinucleotide (FAD), flavin mononucleotide (FMN), riboflavin tetrabutyrate (RTB), salts thereof, and hydrates thereof, with the proviso that:

when the riboflavin derivative comprises FAD, a salt thereof, or a hydrate thereof, a concentration of said FAD, a salt thereof, or a hydrate thereof in the medium is 5 nM to 20 µM, when the riboflavin derivative comprises FMN, a salt thereof, or a hydrate thereof, a concentration of said FMN, a salt thereof, or a hydrate thereof in the medium is 5 nM to 3 µM, and when the riboflavin derivative comprises RTB, a salt thereof, or a hydrate thereof, a concentration of said RTB, a salt thereof, or a hydrate thereof in the medium is 5 nM to 0.5 µM; and wherein the period of time sufficient to degrade an otherwise identical riboflavin-containing medium is at least two weeks at a temperature ranging from 2° C. to 8° C.; and/or wherein said modified medium comprises the riboflavin derivative comprises RTB, a salt thereof, or a hydrate thereof.

10. The method of claim 9, wherein ES or iPS cells when cultured in said modified medium not containing riboflavin and which has been stored for a time and at a temperature sufficient to degrade riboflavin in the otherwise identical medium, have a greater proliferative ability than ES or iPS cells cultured in an otherwise identical medium containing riboflavin which has been stored for the same period of time and at the same temperature.

11. The method of claim 10, wherein the period of time sufficient to degrade the riboflavin in the otherwise identical medium is at least two weeks at a temperature ranging from 2 to 8° C.

12. The method of claim 9, wherein said modified medium comprises the riboflavin derivative comprises FAD, a salt thereof, or a hydrate thereof.

13. The method of claim 9, wherein said modified medium comprises the riboflavin derivative comprises FMN, a salt thereof, or a hydrate thereof.

14. The method of claim 9, wherein said modified medium comprises the riboflavin derivative comprises RTB, a salt thereof, or a hydrate thereof.

15. The method of claim 9, wherein said modified medium further comprises a compound containing Fe2+ in an amount ranging from 0.083 to 0.125 mg/L and a compound containing Zn2+ in an amount ranging from 0.086 to 0.13 mg/L.

16. A method for increasing proliferation of ES or iPS cells comprising: culturing the ES or iPS cells in the medium of claim 1 that has been stored for a period of time sufficient to degrade riboflavin in an otherwise identical medium containing riboflavin instead of the riboflavin derivative, wherein the proliferation of ES or iPS cells in the medium that has been stored is greater than the proliferation of ES or iPS cells when cultured in an otherwise identical medium that has been stored containing riboflavin instead of the riboflavin derivative.

17. The method of claim 16, wherein the medium comprises the riboflavin derivative RTB, a salt thereof, or a hydrate thereof.

18. The method of claim 16, wherein the medium comprises the riboflavin derivative FAD, a salt thereof, or a hydrate thereof.

19. The method of claim 16, wherein the medium comprises the riboflavin derivative FMN, a salt thereof, or a hydrate thereof.

20. The method of claim 16, wherein the medium further comprises a compound containing Fe2+ in an amount ranging from 0.083 to 0.125 mg/L and a compound containing Zn2+ in an amount ranging from 0.086 to 0.13 mg/L.

21. The method of claim 16, further comprising recovering ES or iPS cells.

* * * * *